US008313456B2

(12) United States Patent
Schmaelzle et al.

(10) Patent No.: US 8,313,456 B2
(45) Date of Patent: Nov. 20, 2012

(54) DRUG-TRANSFER DEVICE, DRUG-DELIVERY SYSTEM INCORPORATING THE SAME, METHODS OF FABRICATING THE SAME, AND METHODS OF ENABLING ADMINISTRATION OF A DRUG

(75) Inventors: Philipp Helmut Schmaelzle, Los Altos, CA (US); Scott Albert Uhland, Redwood City, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 12/495,470

(22) Filed: Jun. 30, 2009

(65) Prior Publication Data

US 2010/0331772 A1 Dec. 30, 2010

(51) Int. Cl.
*A61M 31/00* (2006.01)

(52) U.S. Cl. ................ 604/103.01; 604/890.1; 222/592; 222/541.7; 222/553; 234/1

(58) Field of Classification Search .................. 222/592, 222/541.7, 553; 402/8; 604/890.1; 234/1
See application file for complete search history.

(56) References Cited

U.S. PATENT DOCUMENTS 1,596,638 A * 8/1926 Turpel et al. ............... 222/541.9
2,006,963 A * 7/1935 Rollason .................... 222/541.2
3,077,213 A * 2/1963 Germano ...................... 141/358
3,825,179 A * 7/1974 Otsuka ............................ 234/51
4,613,063 A * 9/1986 Wright ..................... 222/153.14
4,961,932 A * 10/1990 Theeuwes ..................... 424/455
5,057,321 A * 10/1991 Edgren et al. ................. 424/473
5,507,277 A * 4/1996 Rubsamen et al. ...... 128/200.14
5,553,740 A * 9/1996 King et al. ........................ 222/1
5,570,818 A * 11/1996 Strong ..................... 222/153.14
6,050,450 A * 4/2000 Gardos ............................. 222/1
6,131,766 A * 10/2000 King et al. ........................ 222/1
6,159,500 A * 12/2000 Demopoulos et al. ........ 424/456
6,291,702 B1 * 9/2001 Becker ............................ 560/51
2004/0176381 A1 * 9/2004 Walsh ........................... 514/251
2005/0118246 A1 * 6/2005 Wong et al. ................... 424/449
2008/0132881 A1 * 6/2008 Wood et al. ................ 604/890.1

* cited by examiner

*Primary Examiner* — Nicholas Lucchesi
*Assistant Examiner* — Scott Medway
(74) *Attorney, Agent, or Firm* — Marger Johhnson & McCollom PC

(57) ABSTRACT

Devices capable of deterring or preventing bulk extraction of drugs from, for example, drug-delivery systems are exemplarily disclosed. In one embodiment, such a device may include a package releasably retaining a drug and an agent. The agent is configured to suppress a physiological effect of the drug when the agent contacts the drug or is coadministered with the drug. The cell package is configured such that an amount of the drug is selectively releasable with respect to the agent when the package is operably proximate to an encoded key. The package, however, may be configured to impose a relatively high likelihood that either the drug will not be accessed or the drug will be contaminated by the agent if access to the contents of the package is sought without the use of an encoded key.

21 Claims, 7 Drawing Sheets

DRUG-TRANSFER DEVICE, DRUG-DELIVERY SYSTEM INCORPORATING THE SAME, METHODS OF FABRICATING THE SAME, AND METHODS OF ENABLING ADMINISTRATION OF A DRUG

RELATED APPLICATION DATA

This application is related to co-pending U.S. patent application Ser. No. 12/495,454, titled "DRUG-TRANSFER DEVICE, DRUG-DELIVERY SYSTEM INCORPORATING THE SAME, METHODS OF FABRICATING THE SAME, AND METHODS OF ENABLING ADMINISTRATION OF A DRUG", filed Jun. 30, 2009 and co-pending U.S. patent application Ser. No. 12/495,485, titled "DRUG-TRANSFER DEVICE, DRUG-DELIVERY SYSTEM INCORPORATING THE SAME, METHODS OF FABRICATING THE SAME, AND METHODS OF ENABLING ADMINISTRATION OF A DRUG", filed Jun. 30, 2009, all of which are herein incorporated by reference for all purposes.

TECHNICAL FIELD

The presently-disclosed embodiments are directed to devices capable of deterring or preventing bulk extraction of drugs from drug-delivery systems, drug-delivery systems incorporating the same, methods of fabricating the same and methods of enabling administration of a drug.

BACKGROUND

Generally, drug-delivery devices (e.g., inhalers, syringes, implantable drug delivery systems, transdermal patches, liquid medicine bottles, eyedroppers, etc.) store drugs until the drugs are required by a user. Often, and even more so in the future as more potent drugs become available, drug-delivery devices are tampered with in order to improperly obtain the drugs stored in the drug-delivery device. This can seriously impede the availability of such drugs to patients and limits business opportunities in the healthcare field. Thus, it would be desirable to provide a means of making it more difficult or impossible to obtain the drug by tampering with the drug-delivery device. It was this understanding that formed the impetus for the embodiments exemplarily described herein.

DETAILED DESCRIPTION OF THE EMBODIMENTS

Figure 1:
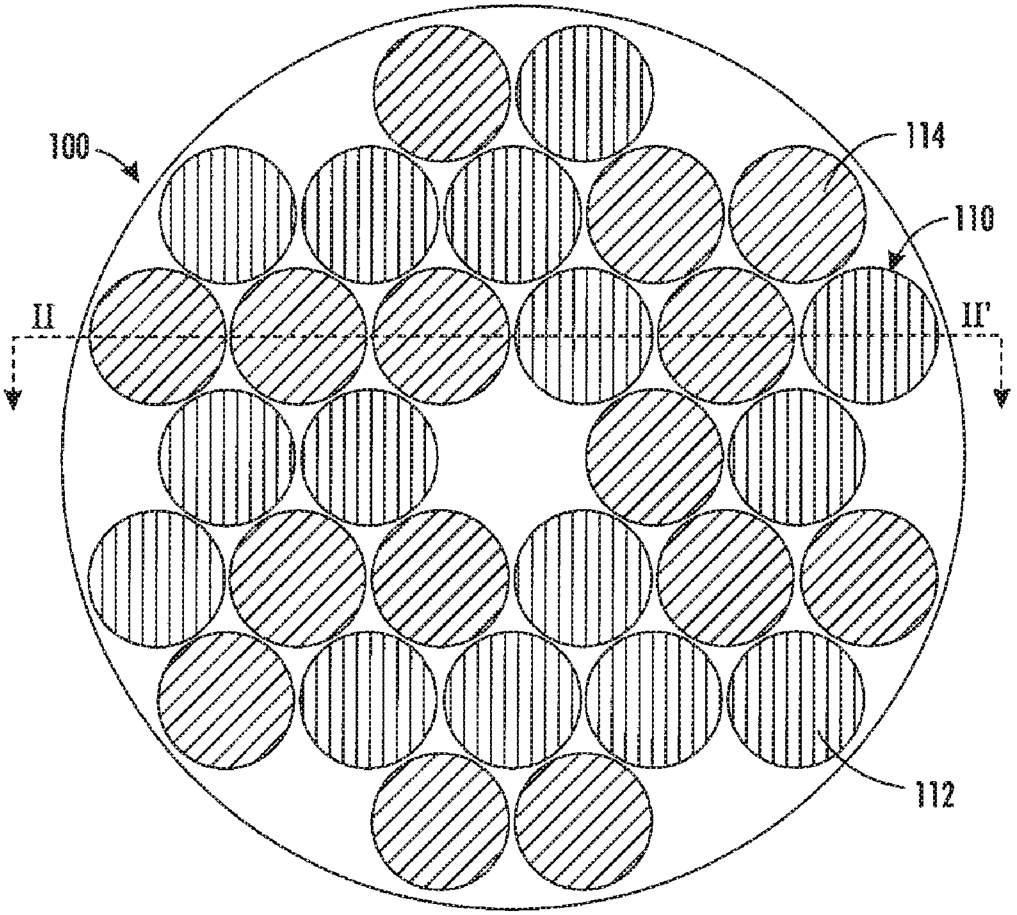
FIG. 1 schematically illustrates an arrangement of cells within a cell package of a drug-transfer device, according to one embodiment.

According to some embodiments exemplarily described herein, a drug-transfer device can be characterized as including a cell package having a first plurality of cells and a drug releasably retained within the first plurality of cells. Cells within the first plurality of cells are disposed at predetermined locations within the cell package. Moreover, the number of cells within the first plurality of cells is less than the total number of cells within the cell package. The cell package is configured such that a predetermined amount of the drug is selectively releasable from at least one cell of the first plurality of cells when the cell package is operably proximate to a key that is encoded with information identifying the predetermined location of the at least one cell within the first plurality of cells. As used herein, a key that is encoded with information identifying the predetermined location of the at least one cell within the first plurality of cells is also referred to as an "encoded key." Likewise, a key that is not encoded with information identifying the predetermined location of the at least one cell within the first plurality of cells is referred to as an "unencoded key."

Because the number of cells within the first plurality of cells is less than the total number of cells within the cell package, the key enables a user to efficiently release a predetermined amount of the drug retained within the drug-transfer device. When the drug is released from the drug-transfer device, the drug can be administered to the user in any suitable manner.

In one embodiment, the cell package further includes a second plurality of cells and an agent releasably retained within the second plurality of cells. Cells of the second plurality of cells are disposed at predetermined locations within the cell package. The agent is configured to suppress a physiological effect of the drug when the agent contacts the drug or is coadministered with the drug. Moreover, the cell package is configured such that a predetermined amount of the drug is selectively releasable from the at least one cell of the first plurality of cells with respect to the agent when the cell package is operably proximate to the encoded key.

If a user attempts to obtain access to the drug retained within the first plurality of cells without use of the key, there is a possibility or a high likelihood, that the agent will be released instead of, or in addition to, the drug. Therefore, the key enables the user to selectively release the drug retained within the drug-transfer device while preventing release of the agent.

As described above, the agent is configured to suppress a physiological effect of the drug when the agent contacts the drug or is coadministered with the drug. Accordingly, the agent may be at least one substance selected from the group consisting of an antagonist (e.g., a competitive antagonist, a non-competitive antagonist, an uncompetitive antagonist, a silent antagonist, a partial antagonist, an inverse antagonist, etc.), a sequestrant that binds to the drug, and a reactant that destroys the drug chemically. Because the agent is configured to suppress a physiological effect of the drug when the agent contacts the drug or is coadministered with the drug, the first plurality of cells contain no (or substantially no) agent. Similarly, the second plurality of cells contain no (or substantially no) drug. As used herein, a cell contains "substantially no" substance (e.g., drug, agent, etc.) when an amount of substance retained within a cell is below some threshold amount (e.g., 1 ppb or less) determined by, for example, a regulatory agency such as the U.S. Food and Drug Administration. Exemplary methods to prevent cross-contamination between the contents of the first plurality of cells and the second plurality of cells are provided below.

In one embodiment, the agent may further be a substance having at least one characteristic (e.g., an optical characteristic, an electrical characteristic, a chemical characteristic, or the like) that matches a corresponding characteristic of the drug. As used herein, a characteristic of the agent "matches" a corresponding characteristic of the drug if the two characteristics are the same or substantially the same. Exemplary optical characteristics include absorption, dispersion, reflection, refraction, transmission, or the like or a combination thereof. Exemplary electrical characteristics include intrinsic charge, conductance, resistance, impedance, dielectric constant, or the like or a combination thereof. Exemplary chemical characteristics include pH, solubility in a solvent, reactivity with a reactant, or the like or a combination thereof. In one embodiment, the agent may be provided as a substance that reacts with the drug in such a manner that the color of the drug/agent reactant is different from the color of the unreacted drug.

In another embodiment, the agent may be a substance that alters at least one characteristic (e.g., a color, an odor, a viscosity, a material phase, or the like or a combination thereof) of the drug. The agent may alter the at least one characteristic of the drug to a degree that can be detected by a person (e.g., a manufacturer/distributor of the drug-transfer device, a manufacturer/distributor of a drug-delivery device, a user of the drug, or the like). In some embodiments, the at least one characteristic of the drug may be altered by the agent in such a manner as to render the drug unattractive to a potential user or abuser of the drug.

In one embodiment, each cell within the cell package has the same or substantially the same size and shape (e.g., circular, elliptical, triangular, square, rectangular, hexagonal, etc.). Thus, cells of the first plurality of cells may have the same or substantially the same size and shape as cells of the second plurality of cells. In another embodiment, each cell within the cell package has one of many predetermined sizes and/or shapes. Thus, each cell of the first plurality of cells and the second plurality of cells may have one of many predetermined sizes and/or shapes, wherein at least some cells of the first plurality of cells have the same or substantially the same size and shape as at least some cells of the second plurality of cells.

In one embodiment, the predetermined amount of drug that is selectively releasable corresponds to a drug dose. As used herein, a "drug dose" refers to the smallest amount of a drug that will have a physiological effect on a user, when administered to the user. As used herein, a "physiological effect" may be a therapeutic effect (i.e., a beneficial or desirable effect on the user) or an adverse effect (i.e., a harmful or undesirable effect on the user). In another embodiment, the predetermined amount of drug that is selectively releasable corresponds to more than a drug dose. In such an embodiment, one or more supplemental devices external to the drug-transfer device may be used to control the amount of drug to be delivered to the user in any manner known in the art.

In one embodiment, each cell within the first plurality of cells retains less than a drug dose. In another embodiment, each cell within the first plurality of cells retains at least a drug dose. In one embodiment, the total amount of drug retained by the first plurality of cells is equal to the predetermined amount of drug. Thus, the first plurality of cells retains the predetermined amount of drug (i.e., a drug dose). In another embodiment, the total amount of drug retained by the first plurality of cells is greater than the predetermined amount of drug. Thus, the first plurality of cells retains the more than the predetermined amount of drug (e.g., potentially, multiple drug doses).

In one embodiment, the cells of the cell package may be disposed in an arrangement having a rotational symmetry when the cell package is viewed in plan view. As used herein, the term "rotational symmetry" refers to an n-fold rotational symmetry, where $n>1$ (e.g., n=2, 3, 4, 6, 8, infinity, etc.). In another embodiment, the cells of the cell package may be disposed in an ordered arrangement having no rotational symmetry (i.e., $n=1$) when the cell package is viewed in plan view. In another embodiment, the cells of the cell package may be disposed in a random arrangement or in a pseudo-random arrangement. As used herein, an arrangement is "pseudo-random" when the cells have no short-range order, but do have a long-range order (e.g., as when cells are disposed in regularly-arranged groups, wherein each group includes randomly-arranged cells) or, alternatively, when the cells have no long-range order, but do have a short-range order (e.g., as when cells are disposed in randomly-arranged groups, wherein each group includes regularly-arranged cells).

Although not illustrated, each cell can, in one embodiment, be generally provided as a band having a contiguous ring shape around the center of the cell package when the cell package is viewed in plan view. The ring shape may be any desired shape (e.g., circular, elliptical, triangular, square, rectangular, hexagonal, etc.), with the center of the ring shape being concentric with the center of the cell package, when the cell package is viewed in plan view. In such an embodiment, the cells are concentrically disposed within the cell package. It will be appreciated, however, that cells may not be concentrically disposed within the cell package. Moreover, the ring shape of one cell may be same as or different from the ring shape of another cell. In one embodiment, the ring shape of one or more of the cells may have a rotational symmetry of $n>1$ when the cell package is viewed in plan view. In another embodiment, the ring shape of one or more of the cells may have no rotational symmetry (e.g., $n=1$) when the cell package is viewed in plan view.

In one embodiment, cell packages may be manufactured such that each cell package includes a unique arrangement of cells. Accordingly, different cell packages may be uniquely identified based on the arrangement of cells included therein. In another embodiment, cell packages may be manufactured in groups such that cell packages within a group have the same arrangement of cells but cell packages of different groups have unique arrangements of cells. In yet another embodiment, cell packages may be manufactured such that cell packages manufactured within only a predetermined period of time (e.g., a week, a month, etc.) have the same arrangement of cells. Accordingly, the arrangement of cells within a manufactured cell package may change periodically over time.

In one embodiment, the first plurality of cells may be disposed within the cell package in an arrangement having a rotational symmetry when the cell package is viewed in plan view. In another embodiment, the first plurality of cells may be disposed within the cell package in an ordered arrangement having no rotational symmetry (i.e., $n=1$) when the cell package is viewed in plan view. In another embodiment, the first plurality of cells may be disposed within the cell package in random arrangement or in a pseudo-random arrangement.

Similarly, the second plurality of cells may be disposed within the cell package in an ordered arrangement having a rotational symmetry when the cell package is viewed in plan view, in an arrangement having no rotational symmetry when the cell package is viewed in plan view, in a random arrangement or in a pseudo-random arrangement.

In one embodiment, a retaining property each cell is degradable in the presence of energy (e.g., light, heat, chemical energy, mechanical energy, an electric field, a magnetic field, etc.). For purposes of discussion herein, whenever a substance (e.g., a drug, an agent, etc.) is retained within a cell, the cell is characterized as being "undegraded." Thus, whenever a substance is released from the cell, the cell is characterized as being "degraded."

In one embodiment, the shape of the cell package itself may have a rotational symmetry (e.g., an n-fold rotational symmetry, where n>1) when viewed in plan view. In another embodiment, the shape of the cell package itself may have no rotational symmetry (i.e., n=1) when viewed in plan view.

In one embodiment, the cell package includes multiple layers of cells (i.e., cell layers). The multiple cell layers may be integrally formed with each other and disposed in a stacked arrangement. As used herein, the term "integrally formed" means that one structure cannot be removed from another structure without rendering one or both structures unsatisfactory for their intended use. Thus, when one cell layer is integrally formed with another cell layer, the two cell layers cannot be removed from one another without degrading one or more cells of the cell layers. In one embodiment, a drug may be releasably retained within only one cell layer while an agent may be releasably retained within only one cell layer. In another embodiment, one cell layer may releasably retain a drug and an agent. It will also be appreciated that the cell package may include only a single cell layer.

In one embodiment, cells within a cell package including multiple cell layers are arranged with respect to each other such that cells in one cell layer are aligned with cells in another cell layer. Cells of different cell layers that are aligned with each other form what is referred to herein as an "aligned cell group." In one embodiment, the substance(s) retained within all of the cells of a cell group may be released together when an encoded key is proximate to a cell package including multiple cell layers, depending upon the configuration of the cell package and/or the key. In another embodiment, the substance(s) retained within a portion of the cells of a cell group may be selectively released together when an encoded key is proximate to a cell package including multiple cell layers, depending upon the configuration of the cell package and/or the key.

To facilitate alignment between cells of different cell layers, the cell layers may include alignment features that cooperate with one another and/or the key. Exemplary alignment features include apertures formed in a cell layer, protrusions extending away from a cell layer, the shape of a cell layer itself (when viewed in plan view), superficial indicia provided on the cell layer (e.g., at an edge thereof), or the like or a combination thereof.

Although the drug-transfer device has been described above as releasably retaining either a drug or an agent, it will be appreciated that the drug-transfer device may releasably retain more than one drug and/or more than one agent. Accordingly, each cell within the first plurality of cells may retain one of a plurality of predetermined drugs. Similarly, each cell within the second plurality of cells may retain one of a plurality of predetermined agents. Further, the drug-transfer device may include at least one of cell that retains a dummy substance instead of a drug or an agent. As used herein, a "dummy substance" refers to a physiologically inactive substance, a GRAS (generally recognized as safe) substance, or the like. In one embodiment, the dummy substrate may further be a substance having at least one characteristic (e.g., an optical characteristic, an electrical characteristic, a chemical characteristic, or the like) that matches a corresponding characteristic of the drug.

According to some embodiments exemplarily described herein, a drug-delivery system can be characterized as including the aforementioned drug-transfer device, a housing configured to retain the drug-transfer device and the key. The key is configured to cause the predetermined amount of drug retained within the cell package of the drug-transfer device to be released when the encoded key is operably proximate to the cell package of the drug-transfer device. The housing is configured such that the drug released from the cell package is deliverable from the cell package retained within the housing to a user.

In one embodiment, the aforementioned drug-transfer device is integrally formed with, or is separable from, the housing. In another embodiment, the key is integrally formed with, or is separable from, the housing. In still another embodiment, the key is integrally formed with, or is separable from the drug-transfer device. As used herein, the term "separable from" means that one structure can be separated from another structure without rendering one or both structures unsatisfactory for their intended use.

As mentioned above, a retaining property each cell in the drug-transfer device is degradable in the presence of energy. In one embodiment, the key includes one or more actuators configured to impart energy to cells within the cell package of the drug-transfer device, to thereby degrade the cells. In one embodiment, the key is proximate to the drug-transfer device when the key is proximate to the drug-transfer device and when energy can be imparted from actuators of the key to cells of the drug-transfer device. Each actuator included in the key may be configured to impart energy in the form of light, heat, chemical energy, mechanical energy, an electric field, a magnetic field, or the like or a combination thereof.

When a cell is degradable in the presence of light, an actuator included in the key may be provided as, for example, a light-emitting diode (LED) configured to emit light at a wavelength (e.g., a UV wavelength) sufficient to induce photodecomposition of the material defining the cell, or the like.

When a cell is degradable in the presence of heat, an actuator included in the key may be provided as, for example, a light-emitting diode (LED) configured to emit light at a wavelength (e.g., an IR wavelength) sufficient to induce thermal decomposition of a material defining the cell, an electronic resistive heating element configured to generate heat sufficient to induce thermal decomposition of the material defining the cell, or the like, or a combination thereof.

When a cell is degradable in the presence of chemical energy, an actuator included in the key may be provided as, for example, a pad having coated on its surface a material sufficient to chemically degrade a material defining the cell, or the like.

When a cell is degradable in the presence of mechanical energy, an actuator included in the key may be provided as, for example, a pin, blade, ultrasonic transducer, etc., configured to mechanically deform a material defining the cell (e.g., by piercing, tearing, etc.), or the like.

When a cell is degradable in the presence of an electrical field, an actuator included in the key may be provided as, for example, one or more electrodes configured to degrade the material defining the cell using an electric field.

When a cell is degradable in the presence of a magnetic field, an actuator included in the key may be provided as, for example, a magnet (e.g., permanent or electromagnet) configured to degrade the material defining the cell using a magnetic field. Exemplary implementations of actuators configured to impart energy in the form of light, heat, chemical energy, mechanical energy, an electric field, a magnetic field, can be found in a discussion regarding the degradation of capsules in copending U.S. application Ser. No. 12/357,108, filed Jan. 21, 2009, entitled "DRUG DEACTIVATION SYSTEM AND METHOD OF DEACTIVATING A DRUG USING THE SAME," which is incorporated by reference herein in its entirety.

In one embodiment, the key includes a plurality of actuators. For example, the number of actuators included in the key may be less than, equal to, or greater than the number of cells (or aligned cell groups) within a cell layer of the drug-transfer device. Each of the plurality of actuators is aligned with a corresponding cell (or aligned cell group) of the drug-transfer device when the key is proximate to the drug-transfer device. As a result, an actuator imparts energy to only a corresponding cell (or aligned cell group) of the drug-transfer device.

In another embodiment, the key includes a single actuator. The single actuator may be configured to be aligned with one or more of the cells (or one or more aligned cell groups) within the drug-transfer device when the key is proximate to the drug-transfer device. As a result, the single actuator imparts energy to one or more cells (or one or more aligned cell groups) within the drug-transfer device.

In one embodiment, the key is operably proximate to the drug-transfer device when the key is proximate to the drug-transfer device and when the key and drug-transfer device are aligned with respect to one another in a predetermined manner. To facilitate alignment between the key and the cell package of the drug-transfer device, the housing may include an alignment feature that cooperates with an alignment feature of the drug-transfer device (e.g., an alignment feature of the cell package), with an alignment feature of the key, or a combination thereof. In another embodiment, the drug-transfer device and the key may include cooperative alignment features, and the housing may not include an alignment feature. Exemplary alignment features include apertures formed in the housing, the drug-transfer device and/or the key, protrusions extending away from the housing, the drug-transfer device and/or the key, the shape of the housing, the drug-transfer device and/or the key (when viewed in plan view), superficial indicia provided on the housing, the drug-transfer device and/or the key (e.g., at an edge thereof), or the like or a combination thereof.

In one embodiment, one or more of the actuators may be provided as a static actuator. As used herein, a "static actuator" imparts energy to a cell (or aligned cell group) within a drug-transfer device automatically, whenever the key is proximate to drug-transfer device. Because a static actuator imparts energy to cell automatically, the location of each static actuator on the key corresponds to a location of a cell within the first plurality of cells in the cell package, when the key is operably proximate to the drug-transfer device. Thus, the location of each static actuator on the key corresponds to the information that is encoded on the key.

In embodiments where an unencoded key includes a plurality of static actuators, the drug-delivery system may further include an encoding unit (not shown) configured to impart energy (e.g., in the form of light, heat, chemical energy, mechanical energy, an electric field, a magnetic field, or the like or a combination thereof) to the one or more of the plurality of static actuators so as to encode the key. The encoding unit may be implemented as, for example, hardware, firmware, and/or software capable of executing any type of computer-executable instructions. The encoding unit may be provided as a device having a dedicated fixed-purpose circuit and/or partially or wholly programmable circuitry. The encoding unit may be integrally formed with the housing or may be provided as a component that is separate from, or is separable from, the housing. Thus, the encoding unit may be used by the manufacturer of the key, the manufacturer of the drug-delivery system, the user of the drug-delivery system, or the like. Generally, the encoding unit may impart energy to the one or more of the plurality of static actuators in response to instructions. The encoding unit may be hard-wired with the instructions. In another embodiment, the encoding unit is configured to receive the instructions (e.g., via an input port thereof). The instructions may be received over a wired or wireless personal area network (PAN), a local area network (LAN), a wide area network (WAN), or the like or a combination thereof. An exemplary method of encoding an unencoded key using an encoding unit is provided below.

In another embodiment, one or more of the actuators may be provided as a dynamic actuator. As used herein, a "dynamic actuator" is electronically driven to impart energy to a cell (or aligned cell group) within a drug-transfer device when the key is proximate to the drug-transfer device. Because a dynamic actuator imparts energy to cell (or aligned cell group) whenever it is driven, the location of a driven dynamic actuator on the key corresponds to a location of a cell within the first plurality of cells in the drug-transfer device when the key is proximate to the cell package. Thus, the location of each driven dynamic actuator on the key corresponds to the information that is encoded on the key.

A dynamic actuator may be electronically driven by a controller that is integrally formed with the key, integrally formed with the housing, or separable from the key and housing. As used herein, a "controller" refers to any type of computer-executable instructions that can be implemented as, for example, hardware, firmware, and/or software. The controller may be provided as a dedicated fixed-purpose circuit and/or partially or wholly programmable circuitry. Generally, the controller drives dynamic actuators of the key in response to instructions. Similar to the encoding unit, the controller may be hard-wired with the instructions. In another embodiment, the controller is configured to receive the instructions (e.g., via an input port thereof). The instructions may be received over a wired or wireless personal area network (PAN), a local area network (LAN), a wide area network (WAN), or the like or a combination thereof.

If a user attempts to obtain access to the drug retained within the first plurality of cells of a cell package using a key that is not encoded with information identifying the predetermined location of at least one cell of the first plurality of cells, there is a possibility, or a high likelihood, that the agent will be released instead of, or in addition to, the drug. Similarly, if a user attempts to obtain access to the drug retained within the first plurality of cells of a drug-transfer device using a key that is encoded with information identifying the predetermined location of at least one cell of the first plurality of cells, but does not properly align the key with respect to the drug-transfer device (i.e., such that the key is not operably proximate to the drug-transfer device), there is a possibility, or a high likelihood, that the agent will be released instead of, or in addition to, the drug. Therefore, providing a key encoded with information identifying the predetermined location of at least one cell of the first plurality of cells to be operably proximate to the cell package enables the user to selectively release the drug retained within the drug-transfer device while preventing release of the agent.

According to some embodiments exemplarily described herein, a method of fabricating a drug-transfer device may include providing a first cell layer including a first plurality of cells within which a drug is retained and providing a second cell layer including a second plurality of cells within which the agent is retained. The first cell layer and the second cell layer may then be coupled together to form a cell package in which the first cell layer and the second cell layer are integrally formed together. Exterior surfaces of the first cell layer and the second cell layer may be cleaned. In one embodiment, exterior surfaces of the first cell layer and the second cell layer may be cleaned prior to final assembly of the drug-transfer device, after final assembly or the drug-transfer device or a combination thereof.

In one embodiment, the first cell layer is provided in an area that is environmentally isolated from another area in which the second cell layer is provided. For example, the first cell layer may be provided by fabricating the first cell layer in an area that is environmentally isolated from all other areas containing any amount of the agent or is contaminated by any amount of the agent. In one embodiment, the first cell layer may be provided by providing a cell sheet, wherein the first plurality of cells is defined within the cell sheet; and coupling a cover sheet to the cell sheet to seal the plurality of cells. In one embodiment, the plurality of cells is hermetically sealed upon coupling the cover sheet to the cell sheet. In one embodiment, fabrication of the first cell layer is concluded upon hermetically sealing the cell layer. The drug may be provided within the first plurality of cells defined by the cell sheet before coupling the cover sheet to the cell sheet. The second cell layer may be provided in a similar manner as discussed above with respect to the first cell sheet, or in a different manner. As used herein, one area is "environmentally isolated" from another area when any portion of the drug or agent (e.g., in solid, liquid, or vapor form) in one area is prevented from entering into the other area. Thus, two areas that may be environmentally isolated from each other may, for example, include two different fabrication lines in the same room, two different rooms in the same building, two different buildings, etc.

Exterior surfaces of the first cell layer and the second cell layer may be cleaned before the first cell layer and the second cell layer are coupled together. Further, an exterior surface of the first cell layer may be cleaned in an area that is environmentally isolated from an area in which the second cell layer is cleaned. This may be beneficial to avoid cross-contamination between the contents of the first plurality of cells and the second plurality of cells.

According to some embodiments exemplarily described herein, a method of enabling administration of a drug may include determining a location of at least one cell of a first plurality of the cells within a drug-transfer device (e.g., provided as exemplarily described above), generating information identifying the determined location of the at least one cell within the drug-transfer device, encoding a key (e.g., provided as exemplarily described above) with the information, providing a user with the drug-transfer device, and providing the key to the user. As described above, a predetermined amount of the drug retained within the at least one cell of the first plurality of cells is selectively releasable when the key is operably proximate to the drug-transfer device and when the key is encoded with the information.

When the user is provided with the drug-transfer device, the drug-transfer device may be integrated with the housing of a drug-delivery system or may be separate from the housing of a drug-delivery system.

In one embodiment, the key may be provided to the user before or after encoding the key with the information. In one embodiment, the key may be provided to the user after the user is provided with the drug-transfer device. In other embodiments, the key may be provided to the user before the user is provided with the drug-transfer device, or simultaneously when the user is provided with the drug-transfer device. In one embodiment the key may be provided to the user through the mail or some suitable courier service.

As mentioned above, the key may include a plurality of static actuators configured to impart energy to cells of the drug-transfer device when the drug-transfer device is proximate to the key. Accordingly, the key may be encoded by deforming at least one of the plurality of static actuators. In this embodiment, a deformed actuator (i.e., a deactivated actuator) is incapable of imparting energy to a cell.

As described above, an actuator may be provided as a dynamic actuator capable of being electronically driven to impart energy to a cell. Accordingly, the key may be encoded by electronically driving the dynamic actuator in response to instructions (e.g., hard-wired in a controller or received at an input port of the controller, as described above). Because the dynamic actuator can be electronically driven, a dynamic actuator can be encoded at a predetermined time after the user has been provided with the drug-transfer device. Also because the dynamic actuator can be electronically driven, a dynamic actuator can be encoded a plurality of times over a predetermined period of time (e.g., over the course of a medical treatment requiring use of the drug).

As mentioned above, the total amount of drug retained by the first plurality of cells may be greater than the predetermined amount of drug. Thus, in one embodiment, the aforementioned method of enabling administration of a drug may further include determining a location of at least one other cell of the first plurality of the cells, generating additional information identifying the determined location of at least one other cell within the drug-transfer device, and encoding the key with the additional information after the predetermined amount of the drug has been released from the at least one cell of the first plurality of cells. Accordingly, a predetermined amount of the drug retained within the at least one other cell of the first plurality of cells is selectively releasable when the key is operably proximate to the drug-transfer device and when the key is encoded with the additional information. Thus, according to this embodiment, multiple drug doses may be released from the same drug-transfer device at different times by encoding the same key multiple times. According to this embodiment, actuators of the key could be provided as dynamic actuators.

As described above, the same key is encoded multiple times to release multiple doses from the same drug-transfer device. In another embodiment, however, an additional key may be encoded with the aforementioned additional information and the additional key may be provided to the user. According to this embodiment, actuators of the additional key could be provided as dynamic actuators, static actuators, or a combination thereof.

Examples of the above-described embodiments of drug-transfer devices, drug-delivery systems, and associated methods of making and using the same to enable administration of a drug, will now be discussed in detail with respect to the accompanying drawings.

Figure 2:
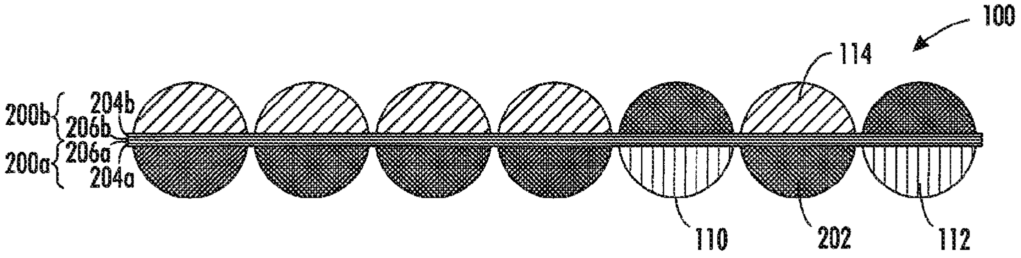
FIG. 2 illustrates a cross-sectional view of the drug-transfer device shown in FIG. 1, taken along line II-II', according to one embodiment.

FIG. 1 schematically illustrates an arrangement of cells within a drug-transfer device according to one embodiment. FIG. 2 illustrates a cross-sectional view of the drug-transfer device shown in FIG. 1, taken along line II-II', according to one embodiment.

Referring to FIG. 1, a drug-transfer device can be characterized as including a cell package 100 including cells 110 disposed at predetermined locations within the cell package 100. A first plurality of the cells 110 (hereinafter the "first plurality of cells") releasably retains a drug 112. A second plurality of the cells 110 (hereinafter the "second plurality of cells") releasably retains an agent 114.

As exemplarily shown in FIG. 1, each cell 110 within the cell package 100 has the same or substantially the same size and shape (e.g., a circular shape). It will be appreciated, however, that each cell 110 within the cell package 100 may be sized differently and/or have a different shape. It will further be appreciated that each cell 110 within the cell package 100 may have one of a plurality of predetermined sizes and/or shapes such that wherein at least some cells 110 of the first plurality of cells have the same or substantially the same size and shape as at least some cells 110 of the second plurality of cells.

As exemplarily shown in FIG. 1, the cells 110 of the cell package 100 are disposed in an arrangement having an n-fold rotational symmetry, where n=6, in viewed in plan view. It will be appreciated, however, that the cells 110 may be arranged in an arrangement having any other n-fold rotational symmetry. It will further be appreciated that the cells 110 may be disposed in an ordered arrangement having no rotational symmetry (i.e., n=1) when the cell package is viewed in plan view, or may be disposed in a random arrangement.

As exemplarily shown in FIG. 1, the first plurality of cells and the second plurality of cells are disposed within the cell package 100 in a random arrangement. Thus, the drug 112 and agent 114 are randomly disposed at a plurality of locations within the cell package 100. It will be appreciated, however, that the first plurality of cells and/or the second plurality of cells may be disposed within the cell package 100 in an any desired arrangement (e.g., ordered arrangement having a rotational symmetry or no rotational symmetry, etc.).

As exemplarily shown in FIG. 1, the shape of the cell package 100 is circular, and therefore, has an infinite rotational symmetry when viewed in plan view. It will be appreciated, however, that the cell package 100 may have any other n-fold rotational symmetry or may have no rotational symmetry when the cell package 100 is viewed in plan view.

Referring to FIG. 2, the cell package 100 includes multiple layers of cells (e.g., first cell layer 200*a* and second cell layer 200*b*) stacked upon each other. The cells 110 are arranged with respect to each other such that cells 110 in the first cell layer 200*a* are aligned with cells 110 in the second cell layer 200*b*. To facilitate alignment between cells 110 of the first cell layer 200*a* and the second cell layer 200*b*, the first cell layer 200*a* and the second cell layer 200*b* may include alignment features (not shown) that cooperate with one another.

As exemplarily shown in FIG. 2, the drug 112 is releasably retained only within the first cell layer 200*a* while the agent 114 is releasably retained only within the second cell layer 200*b*. Thus, the first plurality of cells in the cell package 100 is disposed only within the first cell layer 200*a* and the second plurality of cells in the cell package 100 is disposed only within the second cell layer 200*b*. Providing the first plurality of cells and the second plurality of cells within different cell layers helps to minimize or eliminate cross-contamination of the substances retained within the first plurality of cells and the second plurality of cells.

As exemplarily shown, cells 110 of the first cell layer 200*a* and the second cell layer 200*b* are aligned with respect to each other such that cells 110 retain the drug 112 in the first cell layer 200*a* are aligned with cells 110 that do not retain the agent 114 in the second cell layer 200*b*. Thus, each aligned cell group of the cell package 100 including a cell 110 that retains the drug 112 does not also include a cell that retains the agent 114. It will be appreciated, however, that the cell package 100 may include at least one aligned cell group including cells 110 that retain the drug 112 and the agent 114.

As exemplarily shown in FIG. 2, the first cell layer 200*a* includes a cell sheet 204*a* and a cover sheet 206*a* coupled to the cell sheet 204*a*. The cell sheet 204*a* defines the cells 110 and the cover sheet 206*a* cover the cells 110 defined by the cell sheet 204*a*. Similarly, the second cell layer 200*b* includes a cell sheet 204*b* defining the cells 110 and a cover sheet 206*b* coupled to the cell sheet 204*b* and covering the cells 110 defined therein. The cells 110 are provided as cavities defined by the cell sheet 204*a* and the cell sheet 204*b*. In one embodiment, cover sheets 206*a* and 206*b* are coupled to corresponding cell sheets 204*a* and 204*b* so as to seal the cells 110 defined therein. The cover sheet 206*a* of the first cell layer 200*a* is coupled to the cover sheet 206*b* of the second cell layer 200*b*.

As exemplarily shown in FIG. 2, a third plurality of the cells 110 (hereinafter the "third plurality of cells") releasably retains a dummy substance 202. It will be appreciated, however, that the third plurality of cells may be empty.

Figure 3:
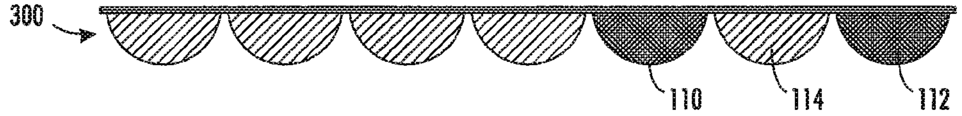
FIGS. 3-5 illustrate cross-sectional views of the drug-transfer device shown in FIG. 1, according to other embodiments.
Figure 4:
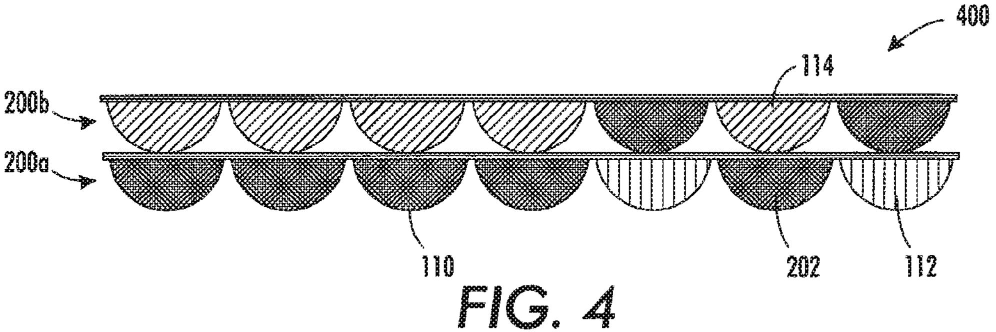
Figure 5:
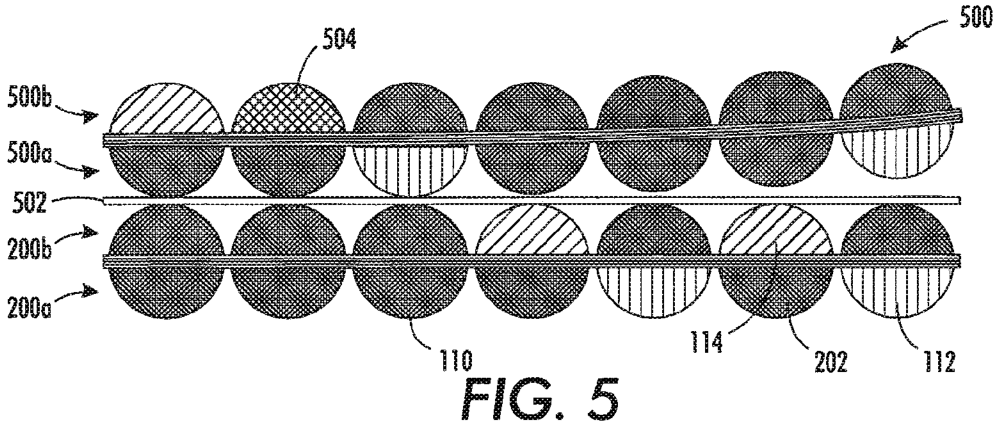

FIGS. 3-5 illustrate cross-sectional views of the drug-transfer device shown in FIG. 1, according to other embodiments.

Referring to FIG. 3, a drug-transfer device can be generally characterized as including a cell package 300 that is similar to the cell package 100 described above with respect to FIGS. 1 and 2. In the illustrated embodiment, however, the cell package 300 may include a single cell layer within which both the drug 112 and the agent 114 are releasably retained. Thus, the first plurality of cells and the second plurality of cells in the cell package 300 are disposed within the same cell layer.

Referring to FIG. 4, a drug-transfer device can be generally characterized as including a cell package 400 that is similar to the cell package 100 described above with respect to FIGS. 1 and 2. In the illustrated embodiment, however, the cover sheet 206*a* of the first cell layer 200*a* is coupled to the cell sheet 204*b* of the second cell layer 200*b*.

Referring to FIG. 5, a drug-transfer device can be generally characterized as including a cell package 500 that is similar to the cell package 100 described above with respect to FIGS. 1 and 2. In the illustrated embodiment, however, the cell package 500 may include a third cell layer 500*a* and a fourth cell layer 500*b* in addition to the first cell layer 200*a* and second cell layer 200*b*. The third cell layer 500*a* and the fourth cell layer 500*b* may each include a cell sheet and a cover sheet as exemplarily described above with respect to FIG. 2. As exemplarily illustrated, the third cell layer 500*a* may be coupled to the second cell layer 200*b* via an interposer member 502. It will be appreciated, however, that the third cell layer 500*a* may be coupled directly to the second cell layer 200*b*, without the use of the interposer member 502.

Cells 110 of the third cell layer 500*a* and the fourth cell layer 500*b* are aligned with respect to each other, and with respect to cells 110 of the first cell layer 200*a* and the second cell layer 200*b*. To facilitate such alignment, the third cell layer 500*a* and the fourth cell layer 500*b* may include alignment features (not shown) that cooperate with one another and/or with alignment features of the first cell layer 200*a* and/or the second cell layer 200*b*.

As exemplarily shown in FIG. 5, the drug 112 is releasably retained only within the first cell layer 200*a* while the agent 114 is releasably retained only within the second cell layer 200*b* and the third cell layer 500*a*. It will be appreciated, however, that the drug 112 may be releasably retained within the fourth cell layer 500*b* in addition to, or instead of the first cell layer 200*a*.

As exemplarily shown in FIG. 5, a fourth plurality of the cells 110 (hereinafter the "fourth plurality of cells") may releasably retain an additional substance 504 (e.g., an additional drug, an additional agent, an additional dummy substance) that is different from the drug 112, the agent 114 and the dummy substance 202.

As exemplarily shown, the cell package 500 includes at least one aligned cell group including multiple cells 110 that retain the drug 112, at least one aligned cell group including a cell 110 that retains the agent 114 and at least one aligned cell group including a cell 110 that retains the additional substance 504. It will be appreciated, however, that at least one aligned cell group of the cell package 500 may include cells 110 retaining any desired combination of the aforementioned substances (e.g., the drug 112, the agent 114, the dummy substance 202 and the additional substance 504) in any desired order.

FIG. 5 illustrates a state in which the cell package 500 is partially fabricated. Specifically, the first cell layer 200*a* is coupled to the second cell layer 200*b*, the third cell layer 500*a* is coupled to the fourth cell layer 500*b*, the interposer member 502 is coupled to the second cell layer 200*b*, and the third cell layer 500*a* is partially coupled to the interposer member 502. To complete fabrication of the cell package 500, the remainder of the third cell layer 500*a* is coupled to the interposer member 502.

Figure 6:
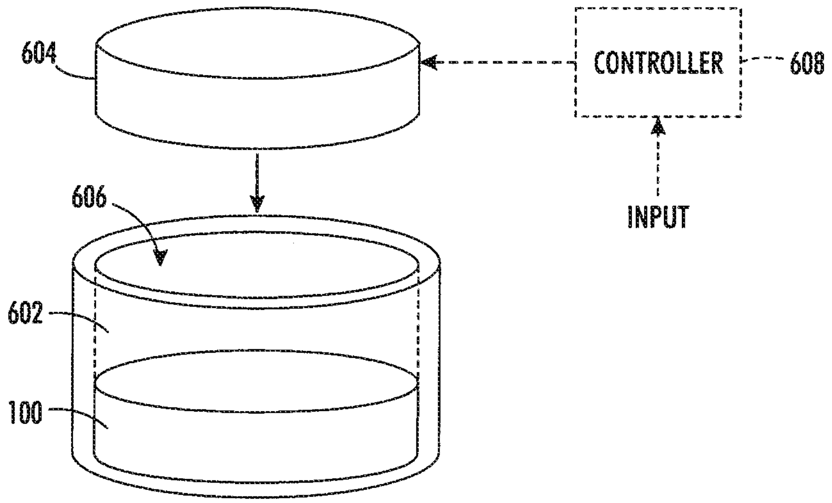
FIGS. 6-8 schematically illustrate drug-delivery systems incorporating a drug-transfer device, according to some embodiments.
Figure 7:
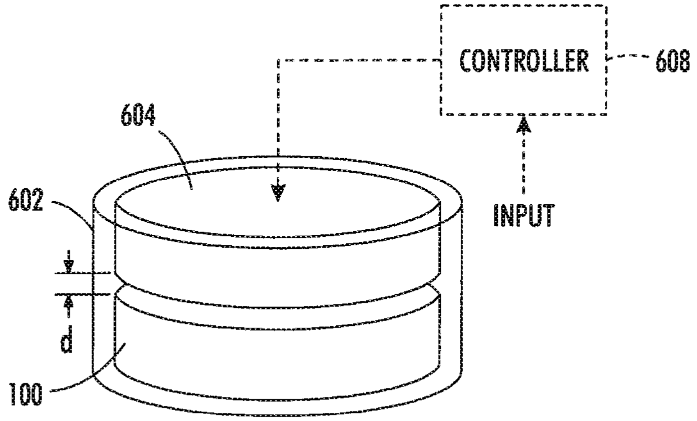
Figure 8:
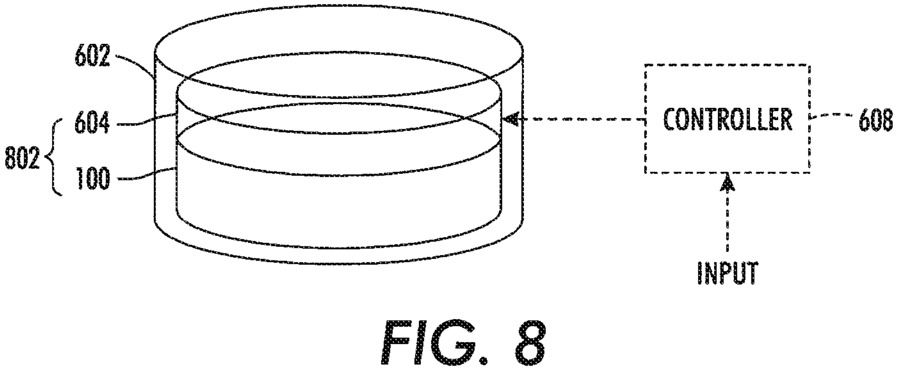

FIGS. 6-8 schematically illustrate drug-delivery systems incorporating a drug-transfer device, according to some embodiments.

Referring to FIG. 6, a drug-delivery system 600 can be characterized as including a drug-transfer device, a housing 602 and a key 604. The housing 602 is configured to retain the drug-transfer device and the key 604. As exemplarily illustrated, the drug-delivery system 600 includes the drug-transfer device exemplarily described above with respect to FIGS. 1 and 2. It will be appreciated, however, that the drug-delivery system 600 may include any drug-transfer device described herein.

The housing 602 is configured such that a predetermined amount of drug, once released from the drug-transfer device, is deliverable to a user (not shown). In one embodiment, the housing 602 is configured to deliver the predetermined amount of drug to the user essentially immediately after the predetermined amount of drug has been released from the drug-transfer device. In another embodiment, the housing 602 is configured to deliver the predetermined amount of drug to the user in a delayed manner after the predetermined amount of drug has been released from the drug-transfer device. For example, the predetermined amount of drug, once released from the drug-transfer device, may be transferred to a reservoir where the drug can be mixed with one or more other substances (e.g., a dummy substance) before being delivered to the user. In another example, the predetermined amount of drug, once released from the drug-transfer device, may be transferred to a semisolid matrix (e.g., an electrophoretic gel, as is known in the art) where the drug can be controllably delivered to the user in the presence of some externally applied energy.

As exemplarily illustrated, the drug-transfer device is integrally formed with the housing 602. In another embodiment, however, the drug-transfer device may be separable from the housing 602. For example, the drug-transfer device may be coupled to, and removed from, the housing 602 via a recess 606 formed in the housing 602.

As exemplarily illustrated, the key 604 is separable from the housing 602. For example, the key 604 may be coupled to, and removed from, the housing 602 via the recess 606. In another embodiment, however, the key 604 may be integrally formed with the housing 602.

To facilitate alignment between the key and the cell package, the housing 602 may include an alignment feature (not shown) that cooperates with an alignment feature of the drug-transfer device, with an alignment feature of the key 604, or a combination thereof. In one embodiment, the alignment feature of the housing 602 may be the shape of the recess 606 when it is viewed in plan view. In such an embodiment, the shape of the recess 606 may have no rotational symmetry when viewed in plan view. In another embodiment, the drug-transfer device and the key 604 may include alignment features that cooperate to ensure proper alignment. In such an embodiment, the housing 602 may not include any alignment feature.

In one embodiment, the key 604 includes one or more actuators configured to impart energy to cells of the drug-transfer device. Energy imparted by the actuators is sufficient to degrade the cells of the drug-transfer device when the drug-transfer device is proximate to the key. In one embodiment, the key 604 includes one or more static actuators, one or more dynamic actuators, or a combination thereof. When the key 604 includes a dynamic actuator, the drug-delivery system 600 may further include a controller 608 configured to drive the dynamic actuator.

As exemplarily illustrated, the controller 608 is separable from the key 604 and housing 602. It will be appreciated, however, that the controller 608 may be integrally formed with the key 604 or the housing 602. As exemplarily illustrated, the controller 608 drives dynamic actuator based on instructions (labeled as "INPUT") received at an input port thereof. Thus, the controller 608 may be configured to receive instructions over a wired or wireless personal area network (PAN) (e.g., via a USB device, Bluetooth enabled device, or the like or a combination thereof), a local area network (LAN) (e.g., via Wi-Fi enabled device, or the like), a wide area network (WAN) (e.g., the Internet), or the like or a combination thereof. It will be appreciated, however, that the controller 608 may be hard-wired with the instructions.

Referring to FIG. 7, a drug-delivery system 700 may be provided as similarly described above with respect to FIG. 6. In the illustrated embodiment, however, both the drug-transfer device and the key 604 are integrally formed with the housing 602.

In one embodiment, the key 604 and the drug-transfer device are positionally fixed within the housing 602 to be spaced apart from each other by a predetermined distance "d" ("d" represents a maximum distance of separation between the key 604 and the drug-transfer device across which energy can be imparted from the key 604 to cells of the drug-transfer device).

In another embodiment, the position of at least one of the key 604 and the drug-transfer device is variable within the housing 602. Thus, the key 604 and the drug-transfer device may have a normally-distant relationship in which the key 604 and the drug-transfer device are spaced apart from each other by a distance greater than "d". However, when the user engages with the housing 602 (e.g., by squeezing the housing 602), the key 604 and the drug-transfer device are brought proximate to each other such that the distance between the key 604 and the drug-transfer device is less than or equal to Referring to FIG. 8, a drug-delivery system 800 may be provided as similarly described above with respect to FIG. 7. In the illustrated embodiment, however, the drug-transfer device includes the key 604 in addition to the cell package 100. Thus, a drug-transfer device 802 may include the key 604 and the cell package 100 integrally formed together. As exemplarily illustrated, the drug-transfer device 802 is integrally formed with the housing 602. In another embodiment, however, the drug-transfer device 802 may be separable from the housing 602.

Figure 9:
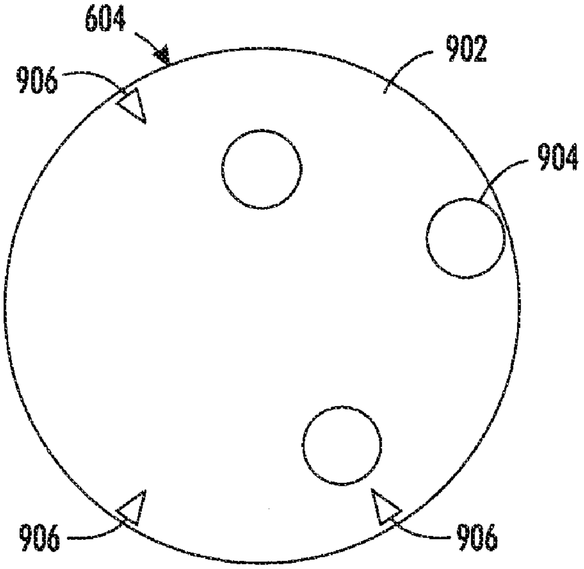
FIGS. 9 and 10 schematically illustrate an arrangement of actuators of a key within a drug-delivery system, according to some embodiments.
Figure 10:
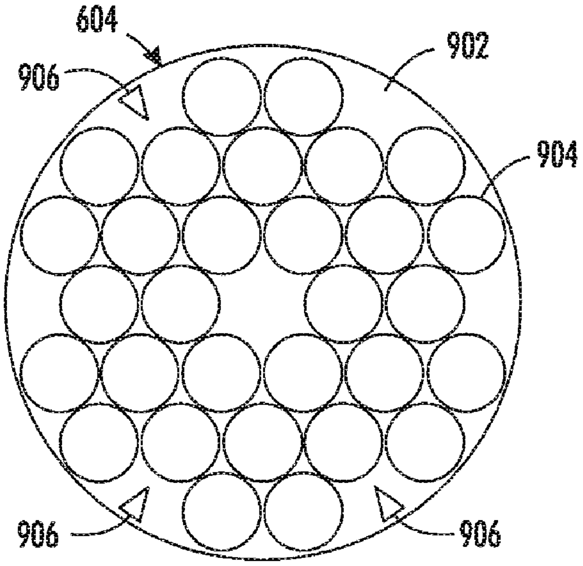

FIGS. 9 and 10 schematically illustrate an arrangement of actuators of a key in the drug-delivery system described with respect to FIG. 6, according to some embodiments.

Referring to FIG. 9, the key 604 may include a key body 902 and a plurality of actuators 904 coupled to the key body 902. The number of actuators 904 coupled to the key body 902 is less than the number of cells 110 within a cell layer of the drug-transfer device. The location of each actuator 904 on the key body 902 is selected such that each of the plurality of actuators 904 will be aligned with a corresponding one of the cells 110 within the drug-transfer device when the key 604 is aligned with the drug-transfer device. Although FIG. 9 illustrates the key 604 as including only three actuators 904, it will be appreciated that the key may include only a single actuator 904, or any desired number of actuators 904.

In one embodiment, the actuators 904 are provided as static actuators. Accordingly, the number of actuators 904 included in the key 604 corresponds to the predetermined amount of drug to be released from the drug-transfer device when the key 604 is proximate to the drug-transfer device. It will be appreciated that the predetermined amount of drug to be released from the drug-transfer device does not necessarily correspond to the amount of drug that is to be ultimately delivered to the user. Supplemental devices external to the key and the drug-transfer device may be used to control the amount of drug to be delivered to the user in any manner known in the art. Such supplemental devices may, for example, be integrally formed with a housing of a drug-delivery system. Further, the location of each actuator 604 relative to the key body 902 is selected such that each actuator 604 will be aligned only with a corresponding cell 110 within the first plurality of cells when the key 604 is operably proximate to the drug-transfer device.

In another embodiment, the actuators 904 are provided as dynamic actuators. Accordingly, the number of actuators 904 included in the key 604 at least minimally corresponds to the predetermined amount of drug to be released from the drug-transfer device when the key is proximate to the drug-transfer device. Further, in embodiments where the number of actuators 904 included in the key 604 corresponds to an amount exceeding the predetermined amount of drug to be released from the drug-transfer device when the key is proximate to the drug-transfer device, the location of each actuator 904 relative to the key body 902 that is driven (e.g., using the controller 608) is selected such that each driven actuator 904 will be aligned with a corresponding cell within the first plurality of cells when the key 604 is operably proximate to the drug-transfer device.

In one embodiment, the key 604 may include alignment features 906 provided as, for example, protrusions extending away from the key body 902. When the key 604 is operably proximate to the drug-transfer device, the protrusions are received within corresponding alignment features of the drug-transfer device (e.g., apertures formed in the cell package of the drug-transfer device). Accordingly, protrusions and the corresponding apertures facilitate alignment between the key 604 and the drug-transfer device. Although FIG. 9 illustrates only three alignment features 906 disposed about the perimeter of the key body 902, it will be appreciated that the key 604 may include any number of alignment features disposed at any portion of the key body 902.

Referring to FIG. 10, the key 604 may be provided as exemplarily discussed above with respect to FIG. 9, but the number of actuators 904 coupled to the key body 902 may be equal to or greater than the number of aligned cell groups within the drug-transfer device. In the illustrated embodiment, actuators 904 are provided as dynamic actuators. Accordingly, the location of each actuator 904 relative to the key body 902 that is driven (e.g., using the controller 608) is selected such that each driven actuator 904 will be aligned with a corresponding cell within the first plurality of cells when the key 604 is operably proximate to the drug-transfer device.

FIGS. 11A, 11B, 12A and 12B illustrate an exemplary method of fabricating the drug transfer device shown in FIGS. 1 and 2, according to one embodiment.

Figure 11A:
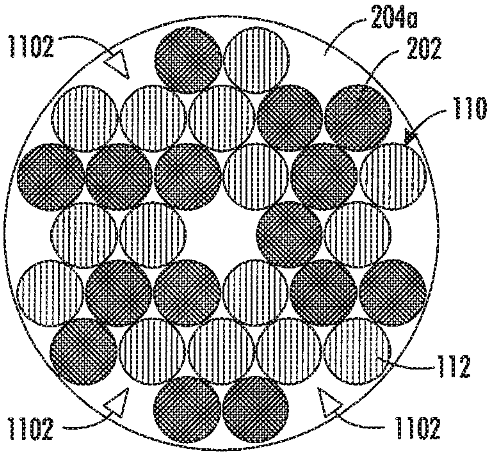
FIGS. 11A, 11B, 12A and 12B illustrate an exemplary method of fabricating the drug transfer device shown in FIGS. 1 and 2, according to one embodiment.
Figure 12A:
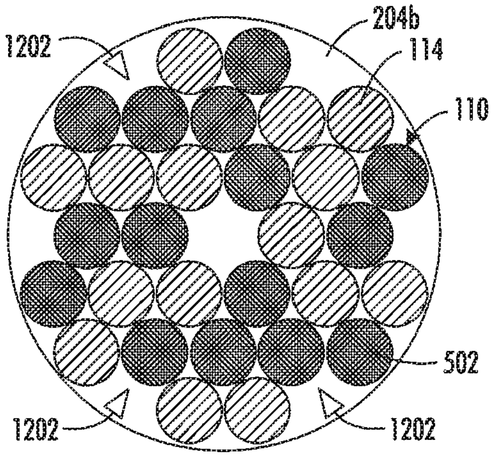

Referring to FIGS. 11A and 12A, each of the cell sheets 204*a* and 204*b* may be provided as a separate polymeric film (e.g., PET), a separate metal film (e.g., Al), or the like or a laminated combination thereof. Cells 110 may be defined within the cell sheets 204*a* and 204*b* using any suitable technique (e.g., using a vacuforming process, an embossing process, or the like or a combination thereof). After forming the cells 110, the drug 112 is provided within the cells 110 defined by the cell sheet 204*a* (i.e., the first plurality of cells) using any suitable technique (e.g., using a pipetting robot, inkjet system, or the like or a combination thereof). Similarly, the agent 114 is provided within the cells 110 defined by the cell sheet 204*b* (i.e., the second plurality of cells) using any suitable technique (e.g., using a pipetting robot, inkjet system, or the like or a combination thereof). Dummy substance 202 may be provided within the third plurality of cells using any suitable technique (e.g., using a pipetting robot, inkjet system, or the like or a combination thereof). Accordingly, all cells 110 of cell sheet 204*a* retain either the drug 112 or the dummy substance 202 and all cells of the cell sheet 204*b* retain either the agent 114 or the dummy substance 202.

Figure 11B:
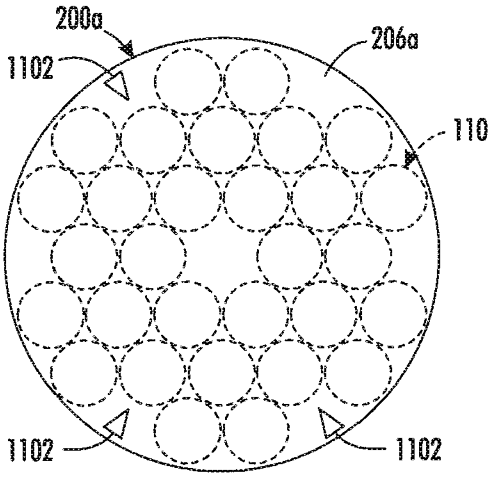
Figure 12B:
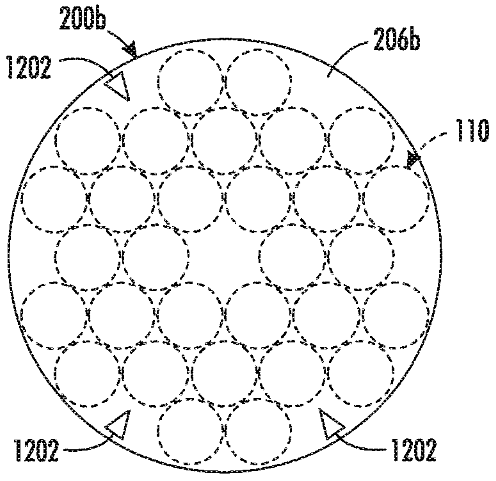

Referring to FIGS. 11B and 12B, the cover sheets 206*a* and 206*b* may be provided as a separate polymeric film (e.g., PET), a separate metal film (e.g., Al), or the like or a laminated combination thereof. The cover sheets 206*a* and 206*b* may be coupled to corresponding cell sheets 204*a* and 204*b* using any known technique (e.g., glue, ultrasonic welding, thermal welding, or the like or a combination thereof). Upon coupling the cover sheets 206*a* and 206*b* to corresponding cell sheets 204*a* and 204*b*, the cells 110 are hermetically sealed and the first cell layer 200*a* and the second cell layer 200*b* are formed.

In one embodiment, the processes of providing the drug 112 within the cells 110 defined by the cell sheet 204*a*, providing the agent within the cells 110 defined by the cell sheet 204*b* and providing the dummy substance 202 within remaining cells 110 defined by the cell sheets 204*a* and 204*b* are performed in a manner that prevents the drug 112 from being provided within cells 110 of the cell sheet 204*b* and in a manner that prevents the agent 114 from being provided within cells 110 of the cell sheet 204*a*. For example, the processes of providing the drug 112 and the dummy substance within the cells 110 defined by the cell sheet 204*a* may be performed in an area (e.g., a first area) that is environmentally isolated from another area (e.g., a second area) in which processes of providing the agent 114 and the dummy substance within the cells 110 defined by the cell sheet 204*b* are performed.

In one embodiment, the processes of coupling the cover sheets 206*a* and 206*b* to corresponding cell sheets 204*a* and 204*b* are performed in a manner that prevents the drug 112 from contaminating any portion of the cell sheet 204*b* and in a manner that prevents the agent 114 from contaminating any portion of the cell sheet 204*a*. For example, the process of coupling the cover sheet 206*a* to cell sheet 204*a* may be performed in an area (e.g., the first area or a third area different from the first area) that is environmentally isolated from another area (e.g., the second area or fourth area different from the second area) in which the process of coupling the cover sheet 206*b* to cell sheet 204*b* is performed.

Although processes have been described above in which cells are defined within cell sheets 204*a* and 204*b* before the drug 112 and agent 114 are provided therein, it will be appreciated that, in some cases (e.g., when the volume of drug 112 or agent 114 to be retained within a cell is very small, when the drug 112 or agent 114 to be retained within a cell does not flow easily or is in a powder form and is to be mixed with a solvent prior to being used by a user, etc.), the drug 112 and/or agent 114 may be provided on corresponding ones of the cell sheets 204*a* and/or 204*b* before the cells are defined therein.

As exemplarily described above, the first cell layer 200*a* is fabricated in an area that is environmentally isolated from all other areas containing any amount of the agent 114 or is contaminated by any amount of the agent 114. Likewise, the second cell layer 200*b* is fabricated in an area that is environmentally isolated from all other areas containing any amount of the drug 112 or is contaminated by any amount of the drug 112. In one embodiment, fabrication of the first cell layer 200*a* and the second cell layer 200*b* is concluded upon hermetically sealing the cell layers as described above. After forming the first cell layer 200*a* and the second cell layer 200*b*, the first cell layer 200*a* and the second cell layer 200*b* are coupled together. In one embodiment, the first cell layer 200*a* and the second cell layer 200*b* are coupled together by coupling the cover sheets 206*a* and 206*b* to each other using any known technique (e.g., glue, ultrasonic welding, thermal welding, or the like or a combination thereof). In order to ensure that the first cell layer 200*a* is properly aligned with the second cell layer 200*b* during the coupling, the first cell layer 200*a* and the second cell layer 200*b* may be provided with complementary alignment features. For example, alignment features 1102 of the first cell layer 200*a* may be provided as at least one aperture formed in the cell sheet 204*a* and/or cover sheet 206*a*, at least one protrusion extending away from the cell sheet 204*a* and/or cover sheet 206*a*, the shape of the first cell layer 200*a* itself (when viewed in plan view), superficial indicia provided on the cell layer 200*a* (e.g., at an edge thereof), or the like or a combination thereof. Similarly, alignment features 1202 of the second cell layer 200*b* may be provided as at least one corresponding protrusion extending away from the cell sheet 204*b* and/or cover sheet 206*b*, at least one corresponding aperture formed in the cell sheet 204*b* and/or cover sheet 206*b*, the shape of a second cell layer 200*b* itself (when viewed in plan view), superficial indicia provided on the second cell layer 200*b* (e.g., at an edge thereof), or the like or a combination thereof. Although FIGS. 11A-12B illustrate only three alignment features 1102 (and three alignment features 1202) disposed about the perimeter of the cell sheet 204*a* (and cell sheet 204*b*) and/or cover sheet 206*a* (and cover sheet 206*b*), it will be appreciated that any cell sheet and any cell layer may include any number of alignment features disposed at any portion thereof.

In one embodiment, the first cell layer 200*a* may include a first through-hole 1104 disposed at a center portion thereof, extending through the cell sheet 204*a* and cover sheet 206*a*. Similarly, the second cell layer 200*b* may include a second through-hole 1204 disposed at a center portion thereof, extending through the cell sheet 204*b* and cover sheet 206*b*. Accordingly, when the first cell layer 200*a* is coupled to the second cell layer 200*b*, the first through-hole 1104 and the second through-hole 1204 are disposed in fluid communication with each other. Depending upon the particular drug-delivery system with which the drug-transfer device is incorporated, the first through-hole 1104 and the second through-hole 1204 may define a channel through which additional substances (e.g., physiological saline and other substances) may flow at one or more times during the life-cycle of the drug-delivery system.

In one embodiment, exterior surfaces of the first cell layer 200*a* and the second cell layer 200*b* may be cleaned using any suitable technique to remove any residual amount of drug 112 or agent 114 that may be present on exterior surfaces thereof. In another embodiment, the processes of cleaning exterior surfaces of the first cell layer 200*a* and the second cell layer 200*b* may be performed in a manner that prevents any residual amount of drug 112 from contaminating any surface of the second cell layer 200*b* and in a manner that prevents any residual amount of the agent 114 from contaminating any surface of the first cell layer 200*a*. For example, the process of cleaning the first cell layer 200*a* may be performed in an area (e.g., the first area, the third area, or a fifth area different from the first area and third area) that is environmentally isolated from another area (e.g., the second area, the fourth area, or a sixth area different from the second area and fourth area) in which the process of cleaning the second cell layer 200*b* is performed. Thus, the cover sheets 206*a* and 206*b* of the first cell layer 200*a* and the second cell layer 200*b* may be coupled to each other after exterior surfaces of the first cell layer 200*a* and the second cell layer 200*b* are cleaned.

Figure 13A:
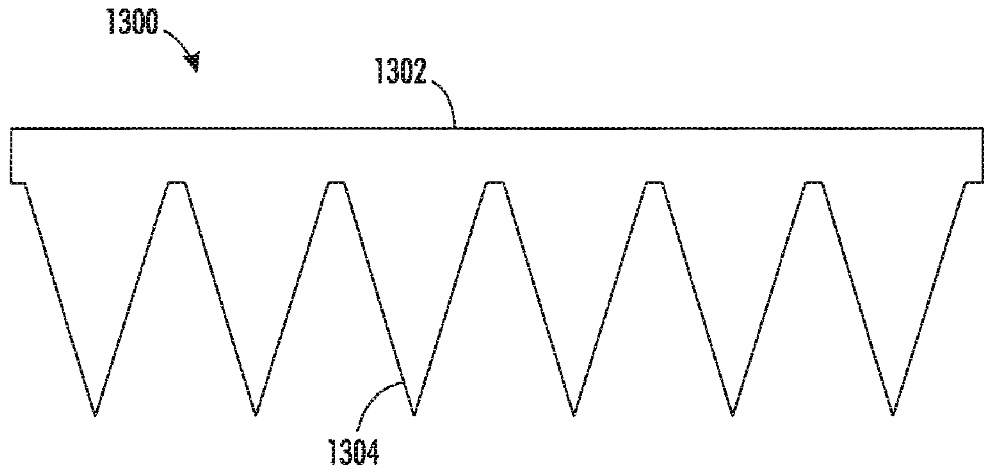
FIGS. 13A and 13B illustrate an exemplary method of encoding a key, according to one embodiment.
Figure 13B:
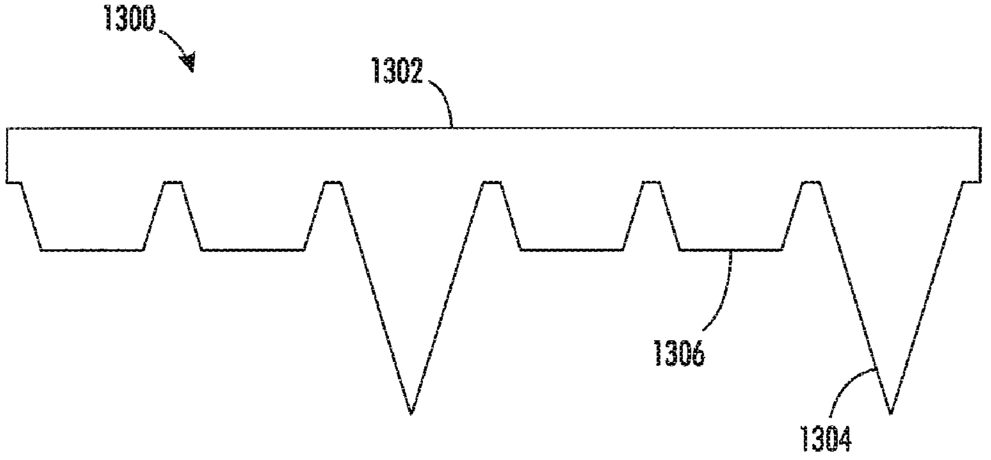

FIGS. 13A and 13B illustrate an exemplary method of encoding a key, according to one embodiment Referring to FIG. 13A, a key 1300 may include a key body 1302 and a plurality of actuators 1304 coupled to the key body 1302. As illustrated, each actuator 1304 is provided as a static actuator such as a pin coupled to the key body 1302. The location of each actuator 1304 included in the key 1300 corresponds to the location of each cell included in a cell layer of a drug-transfer device. The key 1300 may be formed of a polymeric material according to an injection molding process. Accordingly, the key body 1302 and the actuators 1304 may be integrally formed together.

Constructed as described above, the key 1300 may be encoded with information identifying the predetermined location of at least one cell of the first plurality of cells in the drug-transfer device by deactivating (e.g., deforming) selected actuators 1304 that are not arranged a location corresponding to the predetermined location of the at least one cell of the first plurality of cells. Actuators 1304 that have not been deformed have a surface profile (e.g., a sharp pointed profile) that is capable of degrading cells (e.g., by piercing) of a drug-transfer device sufficient. On the other hand, actuators 1304 that have been deformed (i.e., deactivated actuators 1306) have a surface profile (e.g., a dull rounded profile) that is incapable of degrading cells of the drug-transfer device. A selected actuator 1304 may be deformed by permanent thermal deforming. In one embodiment, the permanent thermal deforming may be performed by providing an encoding unit including an array of heating elements (e.g., resistive heating elements), selectively driving predetermined ones of the heating elements to generate heat, and pressing the predetermined ones of the heating elements against the selected actuators 1304. The FIG. 13B illustrates the key 1300 after it has been encoded by deforming the selected actuators 1304 using an encoding unit.

Figure 14A:
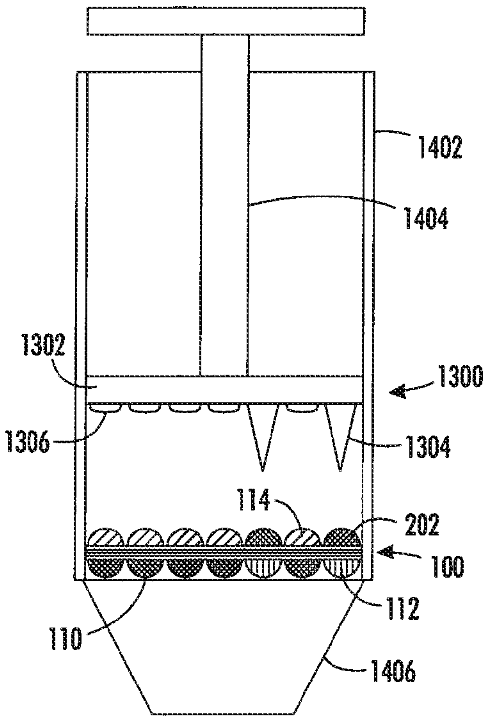
FIGS. 14A and 14B illustrate an exemplary method of administering a drug using a drug-delivery system incorporating a drug-transfer device, according to one embodiment.
Figure 14B:
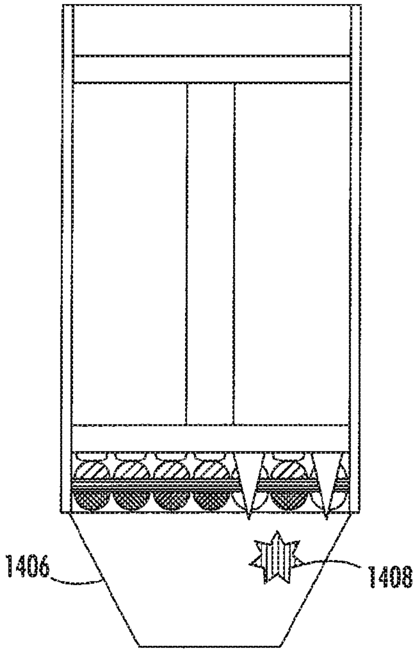

FIGS. 14A and 14B illustrate an exemplary method of administering a drug using a drug-delivery system incorporating a drug-transfer device, according to one embodiment.

Referring to FIG. 14A, a user may be provided with a drug-delivery system including a housing 1402 retaining a drug-transfer device, and a key 1404. As exemplarily illustrated, the housing 1402 is provided as a syringe tube. The housing 1402 may further include a reservoir 1406 where substances released from the drug-transfer device can be mixed with a dummy substance such as physiological saline before being delivered to the user using any known technique (e.g., via a tube, a needle, or the like, or a combination thereof).

The drug-transfer device includes the aforementioned cell package 100 configured described above with respect to FIGS. 1, 2 11A, 11B, 12A and 12B. Accordingly, the drug-transfer device includes a plurality of cells 110, wherein a first plurality of cells releasably retain the drug 112, a second plurality of cells releasably retain the agent 114, and the remaining cells may releasably retain the dummy substance 202.

The key 1404 is provided as a plunger configured to be received within a recess of the housing 1402. The key 1404 is encoded with information identifying the predetermined locations of the first plurality of cells of the drug transfer device (i.e., locations of cells 110 releasably retaining the drug 112 within the cell package 100). The key 1404 is configured as exemplarily described above with respect to FIGS. 13A and 13B. Accordingly, the key 1404 may include a key body 1302, actuators 1304 and deactivated actuators 1306.

As illustrated, the drug-transfer device is integrally formed with the housing 1402 when the user is provided with the housing 1402 and, therefore, has a predetermined alignment with the housing 1402. The integrally formed housing 1402 and drug-transfer device may be provided to the user at a pharmacy. In another embodiment, however, the drug-transfer device may be separable from the housing 1402. In such an embodiment, the drug-transfer device may be provided to the user before or after the user is provided with the housing 1402. As a result, the user may manually insert the drug-transfer device into the recess of the housing 1402. To ensure that the drug-transfer device is properly inserted into the recess of the housing 1402, the shape of the drug-transfer device (when viewed in plan view) may correspond to the shape of the recess of the housing 1402 (when viewed in plan view). Moreover, the shapes of the drug-transfer device and the recess of the housing 1402 may have no rotational symmetry when viewed in plan view.

As illustrated, the key 1404 is separable from the housing 1404 and the drug-transfer device. In one embodiment, the key 1404 may be provided to the user separately from the housing 1402 and/or the drug-transfer device. For example, in embodiments where the integrally formed housing 1402 and drug-transfer device are provided to the user at a pharmacy, the key 1404 may be provided to the user through the mail or some suitable courier service. By providing the key 1404 to the user separately from the integrally formed housing 1402 and drug-transfer device, deviations of the drug towards uses outside the intended use and the user are severely impeded along entire supply chain of the drug-transfer device and/or the drug-delivery system.

Once the user is provided with the integrally formed housing 1402 and drug-transfer device, and is also provided with the key 1404, the user inserts the key 1404 into the recess of the housing 1402. To ensure that the key 1404 is properly inserted into the recess of the housing 1402, the shape of the key 1404 (when viewed in plan view) may correspond to the shape of the recess of the housing 1402 (when viewed in plan view). Moreover, the shapes of the key 1404 and the recess of the housing 1402 may have no rotational symmetry when viewed in plan view. In another embodiment, however, the recess of the housing 1402 may have no alignment feature. In such an embodiment, the key 1404 and the drug-transfer device include cooperative alignment features that can be used to ensure proper alignment of the key 1404 and the drug-transfer device before the key 1404 is proximate to the drug-transfer device.

Referring to FIG. 14B, the user pushes the key 1404 into the housing such that the key 1404 is proximate to the drug-transfer device and the first plurality of cells of the drug-transfer device are degraded. That is, cells 110 releasably retaining the drug 112 within the cell package 100 are pierced by the actuators 1304 having a sharp pointed profile. As illustrated, the aligned cell group including cells that retain the drug 112 also retain the dummy substance 202. The substances released from the drug-transfer device (i.e., the drug 112 and the dummy substance 202) can be mixed together in the reservoir 1406 with physiological saline (e.g., taken in by pulling the key 1404 a predetermined amount out of the housing 1402, away from the drug-transfer device) to form a substance 1408, which includes the drug 112, the dummy substance 202 and the physiological saline, that can then be delivered to the user. The deactivated actuators 1306 have a dull rounded profile and, therefore, do not pierce cells releasably retaining the agent 114. Therefore, the agent 114 remains safely and hermetically retained within the drug-transfer device.

In one embodiment, the aforementioned first through-hole 1104 and second through-hole 1204 are included within the drug-transfer device to define a channel through which the physiological saline may flow into and out of the reservoir 1406.

As exemplarily described above, the total amount of drug 112 retained within the drug-transfer device is equal to a drug dose. Accordingly, the key 1404 is configured to degrade each cell 110 of the first plurality of cells within the cell package 100 and the integrated housing 1402 and drug-transfer device may be disposed of along with the key 1404 after the drug dose has been delivered to the user. It will be appreciated, however, that the total amount of drug 112 retained within the drug-transfer device may be equal to multiple drug doses. Accordingly, the key 1404 may be configured to degrade one or more cells 110 of the first plurality of cells within the cell package 100 and the integrated housing 1402 and drug-transfer device may be retained by the user while the key 1404 may be disposed of after a drug dose has been delivered to the user. Thereafter, the user may be provided with another key configured to degrade one or more other cells 110 of the first plurality of cells within the cell package 100. Accordingly, multiple keys may be provided to a user over a predetermined period of time (e.g., a course of treatment requiring use of the drug 112) while the user retains the housing 1402 and drug-transfer device.

It should be appreciated that reference throughout this specification to "one embodiment," "an embodiment,"

"another embodiment," etc., means that a particular feature, structure or characteristic described in connection with the embodiment is included in at least one embodiment. Therefore, it should be emphasized and appreciated that two or more references to "an embodiment," "one embodiment," "another embodiment," etc., in various portions of this specification are not necessarily all referring to the same embodiment. Furthermore, the particular features, structures or characteristics may be combined as suitable in one or more embodiments.

It will be appreciated that several of the above-disclosed and other features and functions, or alternatives thereof, may be desirably combined into many other different systems or applications. It will also be appreciated that various presently unforeseen or unanticipated alternatives, modifications, variations, or improvements therein may be subsequently made by those skilled in the art which are also intended to be encompassed by the following claims.

What is claimed is:

1. A drug-transfer device, comprising:

a cell package including a first plurality of cells and a second plurality of cells, wherein cells of the first plurality of cells and the second plurality of cells are disposed at predetermined locations within the cell package;

a drug releasably retained within the first plurality of cells; and an agent releasably retained within the second plurality of cells, wherein the agent is configured to suppress a physiological effect of the drug when the agent contacts the drug is at least one of an antagonist, a sequestrant or a destroying reactant, wherein the cell package is configured such that a predetermined amount of the drug is selectively releasable from at least one of the cells of the first plurality of cells with respect to the agent when the cell package is operably proximate to a key encoded with information identifying the predetermined location of the at least one cell of the first plurality of cells within the cell package the key including at least one actuator on a body of a key.

2. The drug-transfer device of claim 1, wherein the cell package further includes a third plurality of cells, the drug-transfer device further comprising:

at least one additional drug, at least one additional agent or a physiologically inactive substance releasably retained within the third plurality of cells.

3. The drug-transfer device of claim 1, wherein the key is separable from the cell package.

4. The drug-transfer device of claim 1, wherein an amount of drug releasably retained within one of the first plurality of cells is less than a dose of the drug.

5. The drug-transfer device of claim 1, wherein the first plurality of cells releasably retains more than a dose of the drug.

6. The drug-transfer device of claim 1, wherein cells of the cell package are disposed in an arrangement having an n-fold rotational symmetry when viewed in plan view, wherein $n>1$.

7. The drug-transfer device of claim 1, wherein the first plurality of cells is disposed in a random arrangement.

8. The drug-transfer device of claim 1, wherein the cell package includes a first cell layer and a second cell layer, wherein the first plurality of cells is included in the first cell layer and wherein the second plurality of cells is included in the second cell layer.

9. The drug-transfer device of claim 1, wherein at least one of an optical characteristic, an electrical characteristic, and a chemical characteristic of the agent matches a corresponding optical characteristic, electrical characteristic, or chemical characteristic of the drug.

10. The drug-transfer device of claim 1, wherein the second plurality of cells does not contain the drug or contains substantially no drug, and the first plurality of cells does not contain the agent or contains substantially no agent.

11. A drug-delivery system, comprising:

a drug-transfer device, comprising:

a cell package including a first plurality of cells and a second plurality of cells, wherein cells of the first plurality of cells and the second plurality of cells are disposed at predetermined locations within the cell package;

a drug releasably retained within the first plurality of cells;

an agent releasably retained within the second plurality of cells, wherein the agent is configured to suppress a physiological effect of the drug when the agent contacts the drug and is at least one of an antagonist, a sequestrant or a destroying reactant; and a housing configured to retain the cell package; and a key configured to cause a predetermined amount of drug retained within at least one of the first plurality of cells to be released selectively with respect to the agent when the key is operably proximate to the drug-transfer device and when the key is encoded with information identifying the predetermined location of the at least one cell of the first plurality of cells, the key including at least one actuator on a body of the key, wherein the housing is configured such that the drug is deliverable from the drug-transfer device to a user via the housing.

12. The drug-delivery system of claim 11, wherein the drug-transfer device is integrally formed with the housing.

13. The drug-delivery system of claim 11, wherein the key is separable from the housing.

14. The drug-delivery system of claim 11, wherein the at least one actuator is configured to impart energy to a cell of the drug-transfer device when the drug-transfer device is proximate to the key and wherein the energy is configured to degrade the cell.

15. The drug-delivery system of claim 14, wherein the at least one actuator on the body of the key is configured to impart energy to a number of cells included within the drug-transfer device that is less than the total number of cells included within the drug-transfer device.

16. The drug-delivery system of claim 14, wherein the location of the at least one actuator in the key corresponds to the information identifying the predetermined location of the at least one cell of the first plurality of cells.

17. The drug-delivery system of claim 16, wherein the at least one actuator is a static actuator configured to impart the energy automatically when the key is proximate to the cell package.

18. The drug-delivery system of claim 17, further comprising an encoding unit configured to impart energy to at least one static actuator in the key to thereby encode the key with the information identifying the predetermined location of the at least one of the first plurality of cells.

19. The drug-delivery system of claim 16, wherein the actuator is a dynamic actuator configured to be electronically driven to impart the energy.

20. The drug-delivery system of claim 19, further comprising a controller coupled to the dynamic actuator, wherein the controller is configured to electronically drive the dynamic actuator based on instructions.

21. The drug-delivery system of claim 20, wherein the controller includes an input port configured to receive the instructions.

* * * * *